United States Patent
Daube et al.

(10) Patent No.: US 8,658,645 B2
(45) Date of Patent: Feb. 25, 2014

(54) USE OF QUINOLONE ANTIBIOTICS

(75) Inventors: Gert Daube, Engelskirchen (DE); Markus Edingloh, Leverkusen (DE); Bernd Stephan, Monheim (DE); Franz Pirro, Langenfeld (DE); Agnès Limet, Boulogne (FR)

(73) Assignee: Bayer Intellectual Property GmbH, Monheim (DE)

( * ) Notice: Subject to any disclaimer, the term of this patent is extended or adjusted under 35 U.S.C. 154(b) by 1894 days.

(21) Appl. No.: 10/567,057

(22) PCT Filed: Aug. 2, 2004

(86) PCT No.: PCT/EP2004/008629
§ 371 (c)(1),
(2), (4) Date: Jun. 26, 2006

(87) PCT Pub. No.: WO2005/018641
PCT Pub. Date: Mar. 3, 2005

(65) Prior Publication Data
US 2007/0082911 A1    Apr. 12, 2007

(30) Foreign Application Priority Data
Aug. 13, 2003 (DE) .................................. 103 37 191

(51) Int. Cl.
*A61K 31/4709* (2006.01)
*A61K 31/4745* (2006.01)
*A61K 6/00* (2006.01)

(52) U.S. Cl.
USPC ...... 514/249; 514/253.08; 514/300; 514/312; 546/223; 546/156; 546/123

(58) Field of Classification Search
None
See application file for complete search history.

(56) References Cited

U.S. PATENT DOCUMENTS 5,808,076 A * 9/1998 Vetter et al. ............... 546/156
2003/0045544 A1   3/2003 Schulz et al.

FOREIGN PATENT DOCUMENTS

WO    WO 97/31001 A1    8/1997

OTHER PUBLICATIONS

Fraatz abstract ( Abstracts of the interscience conference on antimicrobial agents and chemotherapy, 2002, vol. 42, pp. 189).*
Himmler et al abstract (Abstracts of the interscience conference on Antimicrobial Agents and Chemotherapy (2002).*
Bansal, M. B., et al., "Activity of Difloxacin (A-56619) and A-56620 against Clinical Anaerobic Bacteria in Vitro", Antimicrobial Agents and Chemotherapy, 31(4): 619-621 (Apr. 1987).
Coulet, M., et al., "Pharmacokinetics of ibafloxacin Following intravenous and oral administation to healty Beagle dogs", J. Vet. Pharmacol. Therap. 25: 89-97 (2002).
Da Silva, A. D., et al., "Biological Activity and synthetic Metodologies for the Preparation of Fluoroquinolones, a Class of Potent Antibacterial Agents", Current Medicinal Chemistry, 10(1): 21-39 (2003).
Goldstein, E. J. C., et al., In Vitro Activities of a New Des-Fluoroquinolone, BMS 284756, and Seven Other Antimicrobial Agents Against 151 Isolates of *Eikenella corrodens*, Antimicrobial Agents and Chemotherapy, 46(4): 1141-1143 (Apr. 2002).
Granneman, G. R., et al., "Difloxacin Metabolism and Pharmacokinetics in Humans after Single Oral Doses", Antimicrobial Agents and Chemotherapy, 30(5): 689-693 (Nov. 1986).
Hecht, D. W., et al., "Activities of Garenoxacin (BMS-284756) and Other Agents Against Anaerobic Clinical Isolates", Antimicrobial Agents and Chemotherapy, 47(3): 910-916 (Mar. 2003).
McGuirk, P. R., et al. "Synthesis and Structure-Activity Relationships of 7-Diazabicycloalkylquinolones, Including Danofloxacin, a New Quinolone Antibacterial Agent for Veterinary Medicine", J. Med. Chem. 35(4): 611-620 (Feb. 1992).
Slots, J., "Selection of Antimicrobial Agents in Periodontal Therapy", J. Periodont. Res., 37: 389-398 (2002).
Gendron, R., et al., The Oral Cavity as a Reservoir of Bacterial Pathogens for Focal Infections; Mircrobes and Infections, 2000, pp. 897-906.

* cited by examiner

*Primary Examiner* — Savitha Rao

(57) ABSTRACT

The present invention relates to the use of certain quinolone antibiotics for controlling bacterial disorders of the oral cavity, in particular in veterinary medicine.

3 Claims, No Drawings

USE OF QUINOLONE ANTIBIOTICS

This application is a 371 of PCT/EP2004/008629, filed Aug. 2, 2004.

The present invention relates to the use of certain quinolone antibiotics for controlling bacterial infections of the oral cavity, in particular in veterinary medicine.

An in vitro action of various fluoroquinolone antibiotics against anaerobic bacteria including those frequently encountered in infections of the oral cavity has already been described (see: Sobotka I et al.: In vitro activity of moxifloxacin against bacteria isolated from odontogenic abscesses. Antimicrobial Agents and Chemotherapy 46, 4019-4021, 2002; Muller H P et al.: In vitro anti-microbial susceptibility of oral strains of *Actinobacillus actinomycetemcomitans* to seven antibiotics. Journal of Clinical Periodontology 29, 736-742, 2002; Pfister W et al.: Activity of quinolones against anaerobic and capnophilic bacteria in vitro. Deutsche Zahnärztliche Zeitschrift 56, 189-192, 2001; Goldstein E J C et al.: In vitro activities of a new des-fluoroquinolone, BMS 284756, and seven other antimicrobial agents against 151 isolates of *Eikenella corrodens*. Antimicrobial Agents and Chemotherapy 46, 1141-1143, 2002; Hecht D W, Osmolski J R (2003): Activities of garenoxacin (BMS-284756) and other agents against anaerobic clinical isolates. Antimicrobial Agents and Chemotherapy 47, 910-916).

Furthermore, WO 01/45679 describes that fluoroquinolone antibiotics, used locally or topically, are suitable for treating bacterial disorders in particular in the oral cavity, for example during root treatment in dentistry.

Furthermore, ciprofloxacin has been used for the therapy of parodontitis (=periodontal disease). However, a combination therapy with metronidazole is recommended (see: Mombelli A W, van Winkelhoff A J: The systemic use of antibiotics in periodontal therapy. In: Proceedings of the 2$^{nd}$ European Workshop on Periodontology. Chemicals in Periodontics. Eds.: Lang N P, Karring T, Lindhe J. Thurgau, Switzerland, 1996. Quintessenz Books, Berlin, 38-77).

The combination of enrofloxacin and metronidazole for the therapy of parodontitis in dogs and cats has also been described (see: Nielsen D: Clinical Experience with an Enrofloxacin-Metronidazole Combination in the Treatment of Periodontal Disease in Dogs and Cats. In: Proceedings of the Third International Veterinary Symposium on Baytril. Ed. Ford R B. Seville, Spain, 1999, 88-94).

Pradofloxacin and its antibiotic action are described in WO 97/31001.

However, there is still a need for active compounds which, applied systemically on their own or in combination with other antibiotics or chemotherapeutics, are suitable for treating bacterial disorders of the oral cavity. Here, an activity which is as high as possible and an activity spectrum which is as wide as possible against the anaerobic bacteria typical for disorders of the oral cavity are desirable. Preferably, in this manner the customary combination therapy could be dispensed with, monotherapy with only one active compound being sufficient.

Accordingly, the invention relates to the use of
a) 8-cyanoquinolone antibiotics or
b) quinolone antibiotics selected from the group consisting of: garenoxacin, marbofloxacin, ibafloxacin, danofloxacin, difloxacin and orbifloxacin
for preparing medicaments for the systemic treatment of bacterial infections of the oral cavity.

8-Cyanoquinolones are in particular those of the formula (I):

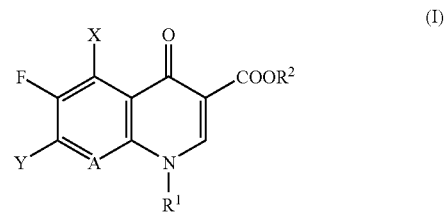

in which
X represents hydrogen, halogen, $C_{1-4}$-alkyl, $C_{1-4}$-alkoxy, $NH_2$,
Y represents radicals of the structure

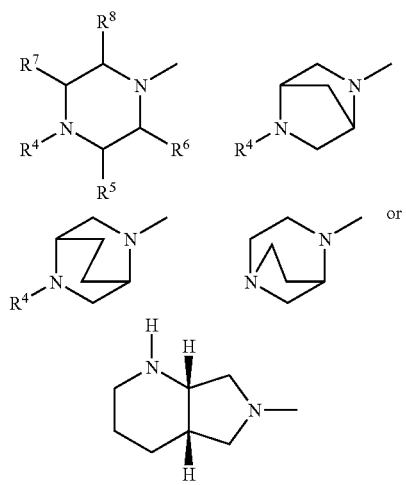

in which
R$^4$ represents optionally hydroxyl- or methoxy-substituted straight-chain or branched $C_{1-4}$-alkyl, cyclopropyl, acyl having 1 to 3 carbon atoms,
R$^5$ represents hydrogen, methyl, phenyl, thienyl or pyridyl,
R$^6$ represents hydrogen or $C_{1-4}$-alkyl,
R$^7$ represents hydrogen or $C_{1-4}$-alkyl,
R$^8$ represents hydrogen or $C_{1-4}$-alkyl,
and
R$^1$ represents an alkyl radical having 1 to 3 carbon atoms, cyclopropyl, 2-fluoroethyl, methoxy, 4-fluorophenyl, 2,4-difluorophenyl or methylamino,
R$^2$ represents hydrogen or optionally methoxy- or 2-methoxyethoxy-substituted alkyl having 1 to 6 carbon atoms and also cyclohexyl, benzyl, 2-oxopropyl, phenacyl, ethoxycarbonylmethyl, pivaloyloxymethyl,
A represents =C(CN),
and their pharmaceutically acceptable salts and hydrates.

Preference is given to compounds of the formula (I) in which
A represents =C—CN,
R$^1$ represents optionally halogen-substituted $C_{1-3}$-alkyl or cyclopropyl,
R$^2$ represents hydrogen or $C_{1-4}$-alkyl, Y represents radicals of the structures

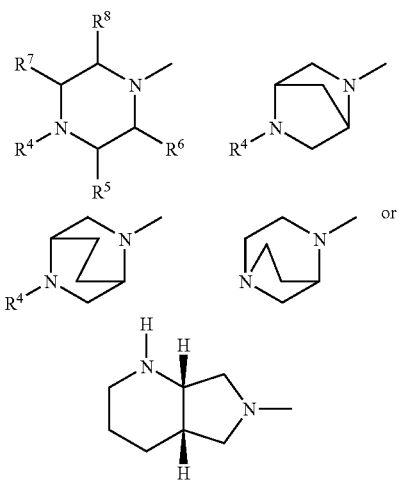

in which
R⁴ represents optionally hydroxyl-substituted straight-chain or branched $C_{1-3}$-alkyl, oxoalkyl having 1 to 4 carbon atoms,
R⁵ represents hydrogen, methyl or phenyl,
R⁷ represents hydrogen or methyl,
R⁶ and R⁸ represent hydrogen,
and their pharmaceutically acceptable hydrates and salts.

Particular preference is given to compounds of the formula (I),
in which
A represents =C—CN,
R¹ represents cyclopropyl,
R² represents hydrogen, methyl or ethyl,
Y represents radicals of the structures

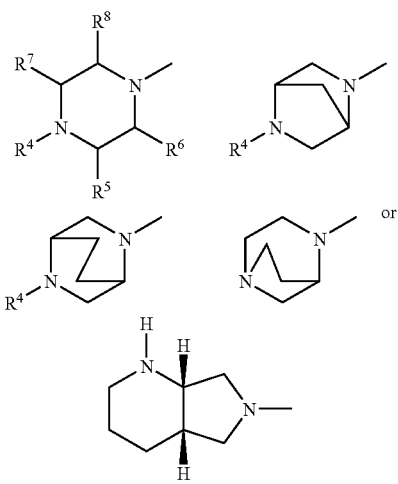

in which
R⁴ represents methyl or optionally hydroxyl-substituted ethyl,
R⁵ represents hydrogen or methyl,
R⁷ represents hydrogen or methyl,
R⁶ and R⁸ represent hydrogen,
and their pharmaceutically acceptable salts and hydrates.

A particularly preferred 8-cyanoquinolone which may be mentioned is pradofloxacin; this compound has the systematic name 8-cyano-1-cyclopropyl-7-((1S,6S)-2,8-diazabicyclo[4.3.0]nonan-8-yl)-6-fluoro-1,4-dihydro-4-oxo-3-quinolinecarboxylic acid and the formula

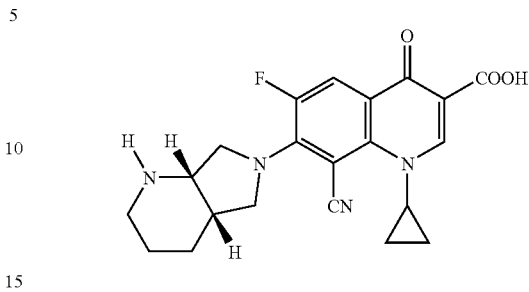

For the purpose of the present invention, pradofloxacin can be used in the form of its pharmaceutically acceptable prodrugs and salts. Also embraced are hydrates and other solvates of these compounds. Suitable prodrugs and salts are described, for example, in WO 97/31001; this document is expressly incorporated herein by reference. It has been found that pradofloxacin has a wide spectrum of antibacterial activity, in particular against germs which play a role in infections of the oral cavity. Accordingly, pradofloxacin is particularly suitable for the monotherapy of bacterial disorders of the oral cavity.

In addition to the 8-cyanoquinolones, other quinolones, too, are suitable for the use according to the invention, namely marbofloxacin (cf., for example, EP-A-259 804), ibafloxacin (cf., for example, EP-A-109 284), danofloxacin (cf., for example, EP-A-215 650), difloxacin (cf., for example, EP-A-131 839) and orbifloxacin (cf., for example, EP-A-242 789). Mention may also be made of garenoxacin (BMS-284756), a 6-defluoroquinolone. For the purposes of this invention, these compounds, too, can be used in the form of their salts, hydrates and prodrugs.

Suitable salts are pharmaceutically acceptable acid addition salts and basic salts.

Pharmaceutically acceptable salts are to be understood as meaning, for example, the salts of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutaminic acid or aspartic acid. It is furthermore possible to bind the compounds according to the invention to acidic or basic ion exchangers. Pharmaceutically acceptable basic salts which may be mentioned are the alkali metal salts, for example the sodium or potassium salts, the alkaline earth metal salts, for example the magnesium or calcium salts; the zinc salts, the silver salts and the guanidinium salts.

Hydrates are understood as including both the hydrates of the fluoroquinolones themselves and the hydrates of their salts.

According to the invention, it is possible to use both the enantiomers and enantiomer mixtures of the quinolones mentioned.

The preparation of the quinolones is known (see, for example, WO 97/31001 for the preparation of pradofloxacin) or can be carried out analogously to known processes.

Disorders of the oral cavity which are caused by bacteria are in particular: gingivitis, parodontitis, stomatitis and oral abscesses.

The bacteria that play a role in these disorders are especially anaerobic bacteria, in particular: *Porphyromonas* spp., *Prevotella* spp., *Bacteroides* spp., *Actinobacillus actinomycetemcomitans*, *Fusobacterium* spp., *Peptostreptococcus* spp., *Eikenella corrodens*, *Capnocytophaga ochracea* and

*Campylobacter rectus*. According to the invention, a good activity against the anaerobic bacteria in question is achieved.

Using the quinolones mentioned above, it is possible to treat bacterial disorders of the oral cavity in humans and animals (productive animals, zoo animals, laboratory animals, experimental animals and pets) by systemic administration.

The productive livestock include mammals, such as, for example, cattle, horses, sheep, pigs, goats, camels, water buffalo, donkeys, rabbits, fallow deer, reindeer, fur-bearing animals, such as, for example, mink, chinchilla, raccoon; birds, such as, for example, chickens, geese, turkeys, ducks, pigeons, ostriches, bird species that are kept at home and in zoos. Also included are productive fish and ornamental fish.

Laboratory animals and experimental animals include mice, rats, guinea pigs, golden hamsters, dogs and cats.

Pets include dogs and cats.

Preference is given to treating mammals, in particular dogs or cats.

Administration can be effected prophylactically as well as therapeutically.

Owing to the wide activity spectrum of the quinolones mentioned—also against anaerobic bacteria—they are particularly suitable for monotherapy.

The active compounds are used directly or in the form of suitable preparations, enterally or parenterally.

The active compounds are administered enterally, for example orally, in the form of powders, suppositories, tablets, capsules, pastes, drinks, granules, drenches, boluses, medicated feed or drinking water. Parenteral administration is effected, for example, in the form of injection (intramuscularly, subcutaneously, intravenously, intraperitoneally) or by implants.

Suitable preparations are:

solutions, such as solutions for injections, oral solutions, concentrates for oral administration after dilution;

emulsions and suspensions for oral administration and for injection; semi-solid preparations;

formulations in which the active compound is incorporated in an oil-in-water or water-in-oil emulsion base;

solid preparations, such as powders, premixes or concentrates, granules, pellets, tablets, boluses, capsules; aerosols and inhalants, shaped articles containing active compound.

Solutions for injection are administered intravenously, intramuscularly or subcutaneously.

Solutions for injection are prepared by dissolving the active compound in a suitable solvent and, if appropriate, adding additives such as solubilizers, acids, bases, buffer salts, antioxidants and preservatives. The solutions are sterile-filtered and drawn off.

The following may be mentioned as solvents: physiologically acceptable solvents, such as water; alcohols, such as ethanol, butanol, benzyl alcohol, glycerol; hydrocarbons, propylene glycol, polyethylene glycols, N-methylpyrrolidone, and mixtures of these.

If appropriate, the active compounds can also be dissolved in physiologically acceptable vegetable or synthetic oils which are suitable for injection.

The following may be mentioned as solubilizers: solvents which enhance dissolution of the active compound in the main solvent, or which prevent its precipitation. Examples are polyvinylpyrrolidone, polyoxyethylated castor oil, polyoxyethylated sorbitan esters.

Preservatives are: benzyl alcohol, trichlorobutanol, p-hydroxybenzoic esters, n-butanol.

Oral solutions are administered directly. Concentrates are administered orally after previously having been diluted to the administration concentration. Oral solutions and concentrates are prepared as described above for the solutions for injection, it being possible to dispense with working under sterile conditions.

It may be advantageous to add thickeners during the preparation. Thickeners are: inorganic thickeners, such as bentonite, colloidal silicic acid, aluminium monostearate, organic thickeners, such as cellulose derivatives, polyvinyl alcohols and their copolymers, acrylates and methacrylates.

Solvents which may be mentioned are: water, alkanols, glycols, polyethylene glycols, polypropylene glycols, glycerol, aromatic alcohols, such as benzyl alcohol, phenylethanol, phenoxyethanol, esters, such as ethyl acetate, butyl acetate, benzyl benzoate, ethers, such as alkylene glycol alkyl ethers, such as dipropylene glycol monomethyl ether, diethylene glycol monobutyl ether, ketones, such as acetone, methyl ethyl ketone, aromatic and/or aliphatic hydrocarbons, vegetable or synthetic oils, DMF, dimethylacetamide, N-methylpyrrolidone, 2-dimethyl-4-oxymethylene-1,3-dioxolane.

Colorants are all colorants which are released for use on animals and which can be dissolved or suspended.

Antioxidants are sulphites or metabisulphites, such as potassium metabisulphite, ascorbic acid, butylhydroxytoluene, butylhydroxyanisole, tocopherol.

Emulsions can be administered orally or as injections.

Emulsions are either of the water-in-oil type or of the oil-in-water type.

They are prepared by dissolving the active compound either in the hydrophobic or in the hydrophilic phase and homogenizing this phase with the solvent of the other phase, with the aid of suitable emulsifiers and, if appropriate, other auxiliaries, such as colorants, absorption enhancers, preservatives, antioxidants, light stabilizers, viscosity-increasing substances.

The following may be mentioned as the hydrophobic phase (oils): paraffin oils, silicone oils, natural vegetable oils, such as sesame seed oil, almond oil, castor oil, synthetic triglycerides, such as caprylic/capric acid biglyceride, triglyceride mixture with the vegetable fatty acids of chain length $C_{8-12}$ or with other specifically selected natural fatty acids, partial glyceride mixtures of saturated or unsaturated fatty acids which may also contain hydroxyl groups, and mono- and diglycerides of the $C_8/C_{10}$-fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}$-$C_{18}$, isopropyl myristate, isopropyl palmitate, caprylic/capric esters of saturated fatty alcohols of chain length $C_{12}$-$C_{18}$, isopropyl stearate, oleyl oleate, decyl oleate, ethyl oleate, ethyl lactate, waxy fatty acid esters, such as dibutyl phthalate, diisopropyl adipate, ester mixtures relating to the latter, etc., fatty alcohols, such as isotridecyl alcohol, 2-octyldodecanol, cetylstearyl alcohol, oleyl alcohol.

Fatty acids, such as, for example, oleic acid and its mixtures.

The following may be mentioned as hydrophilic phase:

water, alcohols, such as, for example, propylene glycol, glycerol, sorbitol and their mixtures.

The following may be mentioned as emulsifiers:

non-ionic surfactants, for example polyoxyethylated castor oil, polyoxyethylated sorbitan monooleate, sorbitan monostearate, glycerol monostearate, polyoxyethyl stearate, alkylphenol polyglycol ethers;

ampholytic surfactants, such as disodium N-lauryl-β-iminodipropionate or lecithin;

anionic surfactants, such as sodium lauryl sulphate, fatty alcohol ether sulphates, the monoethanolamine salt of mono/dialkyl polyglycol ether orthophosphoric esters;

cationic surfactants, such as cetyltrimethylammonium chloride.

The following may be mentioned as other auxiliaries:

viscosity-increasing substances and substances which stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or in the form of an injection. They are prepared by suspending the active compound in a carrier liquid, if appropriate with the addition of further auxiliaries, such as wetting agents, colorants, preservatives, antioxidants, light-stabilizers. Also suitable are suspensions of ion exchangers loaded with the active compound.

Carrier liquids which may be mentioned are all homogeneous solvents and solvent mixtures.

Wetting agents (dispersants) which may be mentioned are the surfactants indicated further above.

Further auxiliaries which may be mentioned are those indicated further above.

Semi-solid preparations can be administered orally. They differ from the above-described suspensions and emulsions only by their higher viscosity.

To prepare solid preparations, the active compound is mixed with suitable carriers, if appropriate with the addition of auxiliaries, and the mixture is formulated as desired.

Carriers which may be mentioned are all physiologically acceptable solid inert substances. Suitable as such are inorganic and organic substances. Examples of such inorganic substances are sodium chloride, carbonates, such as calcium carbonate, bicarbonates, aluminium oxides, silicic acid, clays, precipitated or colloidal silicon dioxide, phosphates.

Examples of organic substances are sugars, cellulose, foods and animal feeds, such as dried milk, animal meals, cereal meals including coarse cereal meals, starches.

Auxiliaries are preservatives, antioxidants, colorants, which have already been indicated further above.

Other suitable auxiliaries are lubricants and gliding agents, such as, for example, magnesium stearate, stearic acid, talc, bentonite, disintegrants, such as starch or crosslinked polyvinylpyrrolidone, binders, such as, for example, starch gelatin or linear polyvinylpyrrolidone, and also dry binders, such as microcrystalline cellulose.

The quinolones used according to the invention can be employed in combination with other active compounds, that is together in one preparation or in different preparations which, if appropriate, can also be administered at different times.

Particular emphasis may be given to combinations with:
other antibiotics/chemotherapeutics, such as beta-lactams (for example amoxicillin, if appropriate in combination with clavulanic acid), cephalosporins (for example cefoperazone); macrolides (for example erythromycin); aminoglycosides (for example gentamicin); tetracyclins (for example doxycyclin) and sulphonamide.
oral antiseptics (for example chlorhexidine)
corticoids (SAIDs=steroidal antiinflammatory drugs), for example prednisolone, methyl-prednisolone, triamcinolone, dexamethasone, betamethasone, flumethasone.

Non-steroidal antiphlogistics (NSAIDs) for example phenylbutazone, naproxen, keto-profen, carprofen, vedaprofen, meclofenamic acid, flunixin, tolfenamic acid, meloxicam.

The other antibiotics/chemotherapeutics listed above are in particular also suitable for a combination which is administered at different times, in a sequential therapy.

Ready-to-use preparations comprise the active compounds in concentrations of in each case 10 ppm to 20 per cent by weight, preferably from 0.1 to 10 per cent by weight.

Preparations which are diluted prior to administration comprise the active compounds in each case in concentrations of from 0.5 to 90 per cent by weight, preferably from 1 to 50 per cent by weight.

In general, it has proved advantageous to administer amounts of about 0.5 to about 50 mg, preferably 1 to 20 mg, of active compound per kg of bodyweight per day, to achieve effective results.

In the mixture with other active compounds, the quinolone antibiotics used according to the invention are present in a ratio of 1:0.1-10 to 1:1-10. Preferred is the ratio 1:5.

The active compounds can also be administered together with the feed or drinking water of the animals.

Feeds and foodstuffs comprise 0.01 to 250 ppm, preferably 0.5 to 100 ppm, of the active compound in combination with a suitable edible material.

Such feeds and foodstuffs can be used both for curative purposes and for prophylactic purposes.

Such a feed or foodstuff is prepared by mixing a concentrate or a premix comprising 0.5 to 30%, preferably 1 to 20% by weight, of an active compound in a mixture with an edible organic or inorganic carrier with customary feeds. Edible carriers are, for example, maize meal or maize and soya bean meal or mineral salts which preferably contain a small amount of an edible oil for preventing the formation of dust, for example maize oil or soya bean oil. The resulting premix may then be added to the complete feed before its being fed to the animals.

EXAMPLES

Example A

Results of In Vitro Studies

Geometric mean of the MIC values (Geometric Mean MIC; GMIC) of anaerobic bacteria isolated from dogs and cats compared to the standard metronidazole (µg/ml). Results of two in vitro studies:

| Genus of the bacteria | N | GMIC pradofloxacin | GMIC metronidazole |
|---|---|---|---|
| Bacteroides | 37 | 0.4 | 0.7 |
| Fusobacterium | 11 | 0.5 | 1 |
| Peptostreptococcus | 4 | 0.4 | 0.8 |
| Porphyromonas | 8 | 0.1 | 0.3 |
| Prevotella | 25 | 0.2 | 0.4 |

Example B

Clinical Study for the Indication Parodontitis

The study was carried out using 16 female beagles. Pradofloxacin was administered in a dose of 3 mg/kg once per day over a period of seven days.

The treatment with pradofloxacin resulted in a significant reduction (p=0.02) of the periodontal pocket depth (loss of attachment).

After the treatment with pradofloxacin had ended, the total number of anaerobic bacteria in the periodontal pockets had been reduced significantly (p<0.0001). This was true even three weeks after the treatment, on day 28 (p=0.0007).

Example C

In Vitro Study

In this study, in each case two strains of the parodontitis-causing bacteria were isolated, and their sensitivity to pradofloxacin was determined in vitro (MIC µg/ml). The results were as follows:

*Actinobacillus actinomycetemcomitans*: MIC<0.25 (both strains)
*Eikenella corrodens*: MIC<0.25 (both strains)
*Capnocytophaga ochracea*: MIC<0.25 (both strains)
*Porphyromonas gingivalis*: MIC<0.25 (both strains)
*Porphyromonas canons*: MIC<0.25 (both strains)
*Porphyromonas cangingivalis*: MIC=0.5 and MIC=1
*Porphyromonas cansulci*: MIC<0.25 (both strains)
*Prevotella intermedia*: MIC<0.25 (both strains)
*Fusobacterium nucleatum*: MIC=0.5 and MIC=1
*Campylobacter rectus*: MIC<0.25 (both strains)

The invention claimed is:

1. A method for the systemic treatment of bacterial infections of the oral cavity comprising systemically treating a human or an animal in need thereof with an effective amount of pradofloxacin.

2. The method of claim 1, wherein the infections of the oral cavity are gingivitis, stomatitis, parodontitis and/or abscesses of the oral cavity.

3. The method of claim 1, wherein the bacterial infections are mainly caused by bacteria of the group consisting of *Porphyromonas* spp., *Prevotella* spp., *Bacteroides* spp., *Actinobacillus actinomycetemcomitans*, *Fusobacterium* spp., *Peptostreptococcus* spp., *Eikenella corrodens*, *Capnocytophaga ochracea*, *Campylobacter rectus*.

* * * * *